US012690775B2

(12) United States Patent
Sheridan et al.

(10) Patent No.: US 12,690,775 B2
(45) Date of Patent: Jul. 28, 2026

(54) WEARABLE PHOTOPLETHYSMOGRAPHY DEVICE FOR DETECTING CLINICAL DECOMPENSATION BASED ON HEART RATE VARIABILITY

(71) Applicant: OREGON HEALTH & SCIENCE UNIVERSITY, Portland, OR (US)

(72) Inventors: David Sheridan, Portland, OR (US); Steven D. Baker, Portland, OR (US); Ryan Dehart, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 433 days.

(21) Appl. No.: 18/245,684

(22) PCT Filed: Sep. 16, 2021

(86) PCT No.: PCT/US2021/050682
§ 371 (c)(1),
(2) Date: Mar. 16, 2023

(87) PCT Pub. No.: WO2022/060991
PCT Pub. Date: Mar. 24, 2022

(65) Prior Publication Data
US 2023/0346234 A1 Nov. 2, 2023

Related U.S. Application Data

(60) Provisional application No. 63/079,176, filed on Sep. 16, 2020.

(51) Int. Cl.
*A61B 5/024* (2006.01)
*A61B 5/00* (2006.01)

*A61B 5/11* (2006.01)
*G16H 50/20* (2018.01)

(52) U.S. Cl.
CPC ........ *A61B 5/02405* (2013.01); *A61B 5/0022* (2013.01); *A61B 5/02416* (2013.01); *A61B 5/1118* (2013.01); *A61B 5/681* (2013.01); *A61B 5/7203* (2013.01); *A61B 5/746* (2013.01); *G16H 50/20* (2018.01)

(58) Field of Classification Search
None
See application file for complete search history.

(56) References Cited

U.S. PATENT DOCUMENTS

| | | | |
|---|---|---|---|
| 10,398,381 B1 * | 9/2019 | Heneghan ............ | A61B 5/6824 |
| 2015/0109124 A1 * | 4/2015 | He ........................ | G06F 3/0481 |
| | | | 340/539.12 |
| 2015/0173631 A1 * | 6/2015 | Richards .............. | A61B 5/7282 |
| | | | 600/479 |

(Continued)

*Primary Examiner* — Michael W Kahelin
(74) *Attorney, Agent, or Firm* — Foster Garvey PC

(57) ABSTRACT

Disclosed are clinical decompensation monitoring platforms and methods. An example platform includes a wearable device to acquire photoplethysmography (PPG) waveform data representing a person's heart rate variability (HRV). Also disclosed are methods for collecting and verifying the HRV data, scoring and selecting optimal segments of HRV data for further processing that entails detecting clinically significant changes in a high frequency (HF) component, and passively monitoring clinical decompensation for providing patient feedback with individualized coping mechanisms.

14 Claims, 6 Drawing Sheets

PERIODICALLY ACQUIRING THE PPG WAVEFORM DATA 302

PERFORMING BEAT DETECTION ON THE PPG WAVEFORM DATA 304

VERIFYING DETECTED BEATS BY CHECKING MOTION DATA MEASURED BY THE WEARABLE PPG DEVICE AND COMPARING THE DETECTED BEATS TO A CORRESPONDING REFERENCE SIGNAL CONFIGURED TO DETERMINE COMMON FIDUCIALS REPRESENTING A REPEATING CARDIOGENIC ARTIFACT 306

IN RESPONSE TO THE VERIFYING, CALCULATE A HEART RATE VARIABILITY (HRV) METRIC FROM THE DETECTED BEATS 308

COMPARE THE HRV METRIC TO A CLINICAL DECOMPENSATION THRESHOLD SO AS TO DETECT THE CLINICAL DECOMPENSATION IN THE PERSON 310

IN RESPONSE TO DETECTING THE CLINICAL DECOMPENSATION, PROVIDE A NOTIFICATION 312

(56)                    References Cited

U.S. PATENT DOCUMENTS

2017/0251987 A1*   9/2017   Collier ................... A61B 5/165
2017/0319122 A1*  11/2017   Wild ..................... G06Q 50/22
2018/0303357 A1*  10/2018   Galeev ................ A61B 5/4035
2020/0100693 A1*   4/2020   Velo ...................... G16H 50/20
2023/0081751 A1*   3/2023   Chatham ............... A61B 5/681
                                                              600/479

* cited by examiner

| PERIODICALLY ACQUIRING THE PPG WAVEFORM DATA 302 |

| PERFORMING BEAT DETECTION ON THE PPG WAVEFORM DATA 304 |

| VERIFYING DETECTED BEATS BY CHECKING MOTION DATA MEASURED BY THE WEARABLE PPG DEVICE AND COMPARING THE DETECTED BEATS TO A CORRESPONDING REFERENCE SIGNAL CONFIGURED TO DETERMINE COMMON FIDUCIALS REPRESENTING A REPEATING CARDIOGENIC ARTIFACT 306 |

| IN RESPONSE TO THE VERIFYING, CALCULATE A HEART RATE VARIABILITY (HRV) METRIC FROM THE DETECTED BEATS 308 |

| COMPARE THE HRV METRIC TO A CLINICAL DECOMPENSATION THRESHOLD SO AS TO DETECT THE CLINICAL DECOMPENSATION IN THE PERSON 310 |

| IN RESPONSE TO DETECTING THE CLINICAL DECOMPENSATION, PROVIDE A NOTIFICATION 312 |

FIG. 3

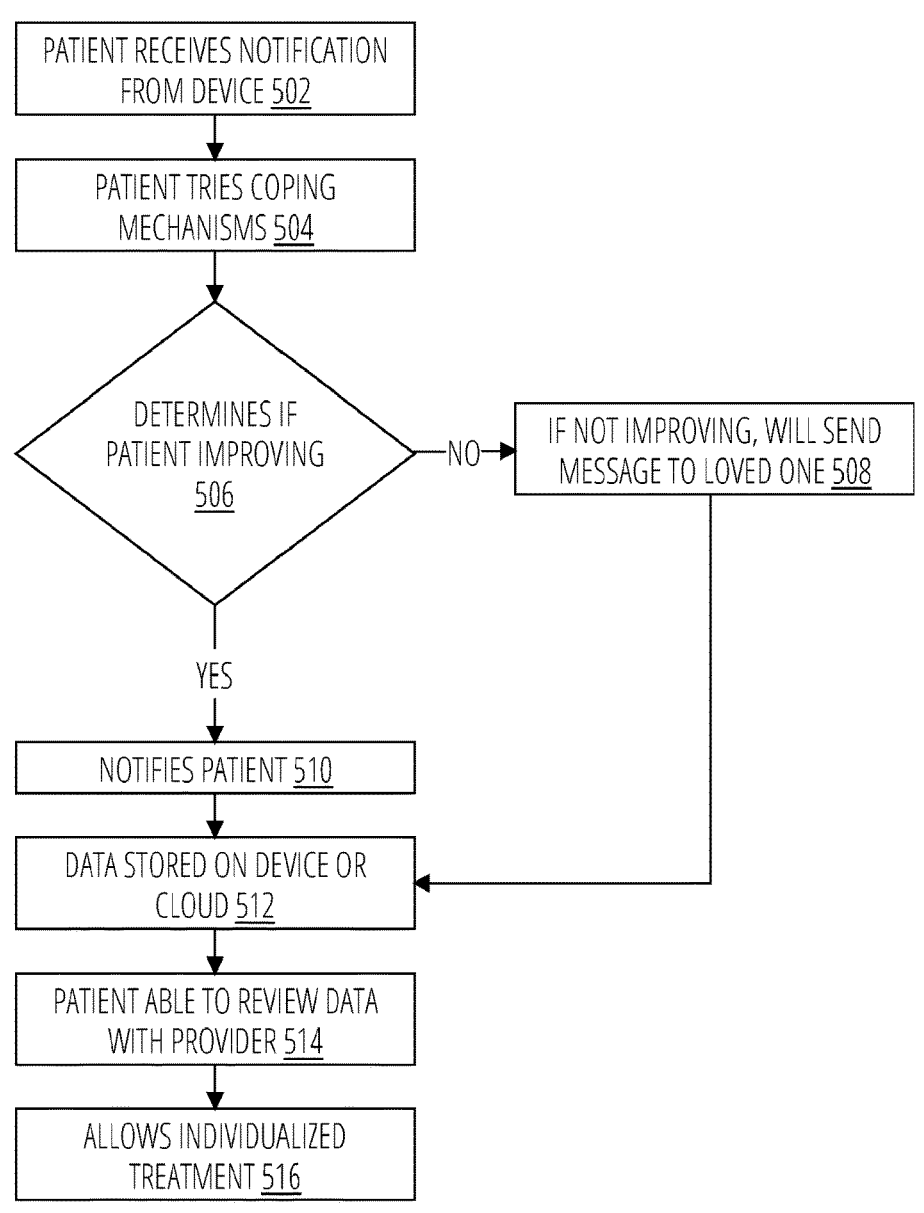
PATIENT RECEIVES NOTIFICATION
FROM DEVICE 502
PATIENT TRIES COPING
MECHANISMS 504
DETERMINES IF
PATIENT IMPROVING
506
NO → IF NOT IMPROVING, WILL SEND
MESSAGE TO LOVED ONE 508
YES
NOTIFIES PATIENT 510
DATA STORED ON DEVICE OR
CLOUD 512
PATIENT ABLE TO REVIEW DATA
WITH PROVIDER 514
ALLOWS INDIVIDUALIZED
TREATMENT 516
FIG. 5

WEARABLE PHOTOPLETHYSMOGRAPHY DEVICE FOR DETECTING CLINICAL DECOMPENSATION BASED ON HEART RATE VARIABILITY

RELATED APPLICATION

The present application is a national phase entry under 35 U.S.C. § 371 of International Application No. PCT/US2021/050682 filed Sep. 16, 2021, which designates the United States of America, which claims priority to U.S. Provisional Patent Application No. 63/079,176, filed Sep. 16, 2020, the entire disclosures of each of these applications are hereby incorporated by reference in their entireties and for all purposes.

FEDERALLY SPONSORED RESEARCH OR DEVELOPMENT

This invention was made with government support under K12 HL133115 awarded by the National Institutes of Health. The government has certain rights in the invention.

TECHNICAL FIELD

This disclosure relates generally to analysis of heart rate variability (HRV) data and, more particularly, to identifying changes in HRV metrics associated with clinical decompensation.

BACKGROUND INFORMATION

A pulse monitor is an electronic or electromechanical sensor that measures physiological difference that occur due to a heartbeat and convert those measurements to an electrical signal that allows accurate detection of a pulse. For example, pulse monitors include a photoplethysmography (PPG), an electrocardiograph (ECG), or a pressure transducer in a blood pressure cuff. PPG is an optically obtained plethysmogram that can be used to detect blood volume changes occurring during systole and diastole. PPG employs a light source and photodetector placed against the skin to measure microcirculatory changes in blood volume allowing for beat to beat detection. ECG produces a relatively clear signal with less motion artifact than measurements made on an extremity.

Clinical decompensation is the functional deterioration of a structure or system that had been previously working with the help of allostatic compensation. Clinical decompensation may occur due to fatigue, stress, illness, or old age. When a system is compensated, it is able to function despite stressors or defects. Decompensation describes an inability to compensate for these deficiencies. It is a general term commonly used in medicine to describe a variety of situations.

HRV is a measurement that evaluates the very small beat-to-beat time interval (BBI) difference produced by the heart. This is different than heart rate, which is the number of beats over a one-minute time period. HRV has been used for years as a marker of multiple conditions ranging from cardiac disease to mental health. It has gained popularity as prior science has shown HRV to be a marker for the health of the autonomic nervous system. This has opened up the realm of possibilities of this measure to give new insights into areas of medicine that were once thought difficult to examine, especially the case for mental health or clinical decompensation.

There exist metrics of HRV focused on the parasympathetic branch of the nervous system, and separate metrics are focused on the sympathetic branch of the nervous system. For example, the high frequency (HF) component of HRV in the frequency domain and the Root Mean Squared of Successive Differences (RMSSD) in the time domain are postulated to correlate with the activity of parasympathetic nervous system.

HRV has traditionally been measured by chest wall ECG. Studies to date have been limited by measurements at a single time point and confined to laboratory settings where patients are connected to cardiac leads.

Technology currently exits to obtain HRV through devices using PPG. Many smartwatches incorporate PPG technology. Smartwatches represent a $5 billion industry, and estimates show that one in six adults in the United States owns a smartwatch. The widespread use and incorporation of PPG in smartwatches, therefore, makes this a widely available technology to leverage if a way can be found to provide clinically-reliable HRV metrics within the constraints of a smartwatch.

SUMMARY OF THE DISCLOSURE

Passive monitoring of stress dysregulation with objective physiologic parameters obtained through intermittent and adaptive PPG is disclosed. Also disclosed are techniques for identifying changes in HRV metrics associated with clinical decompensation. In some embodiments, smartwatch technology generates PPG data to facilitate continuous monitoring and feedback. Monitoring with specific target levels, feedback mechanisms, and data collection retrievable through a cloud-based system are also disclosed. This allows for early intervention before a patient may consciously recognize things are wrong, so as to improve just-in-time therapies.

The monitoring and analysis may be accomplished with wearable technology, e.g., by virtue of intermittent high-power PPG actuation. In some embodiments, the resolution (either bits per sample, sample rate, or filters) or signal-to-noise ratio (SNR) of HRV data is changed as the patient state is determined to be at a higher risk and/or if patient motion has precluded obtaining clean data to minimize the likelihood of beat-picking errors. Resolution may be changed via bits/sample, sample rate, or filters. SNR may be changed by modifying parameters of the A/D converter, for example to average more samples.

In some embodiments, PPG frequency data provides for a measure of the HF component of HRV in about one to five-minute intervals, for every hour or other preconfigured period, during the day and optionally during the night. Other embodiments may prefer longer intervals between measurements or longer measurements. The raw data is optionally filtered to remove spurious results associated with movement observed by an accelerometer or a similar device. Using a combination of inputs, including time since last measurement and activity level determined from the accelerometer, the system preferentially acquires data during relatively stationary periods, for example, less than 0.05 G for at least 8 of the last 10 samples. This allows for improved detection of HRV by removing data obtained in high-movement activities that significantly impact data quality. It also conserves energy by not acquiring data that are likely unusable or unstable.

Finally, using a combination of time- and frequency-domain techniques, segments with relatively short breaks can be melded together maintaining the original HRV statistics of the original data, for example, RMSSD, LF, MF, and HF. Additional aspects and advantages will be apparent from the following detailed description of embodiments, which proceeds with reference to the accompanying drawings.

BRIEF DESCRIPTION OF THE DRAWINGS

To easily identify the discussion of any particular element or act, the most significant digit or digits in a reference number refer to the figure number in which that element is first introduced.

FIG. 3 is a flow chart showing a method of processing PPG waveform data from a wearable PPG device, according to one embodiment.

FIG. 5 is a flow chart of a process for stress dysregulation monitoring and providing patient feedback, according to one embodiment.

DETAILED DESCRIPTION OF EMBODIMENTS

Figure 1:
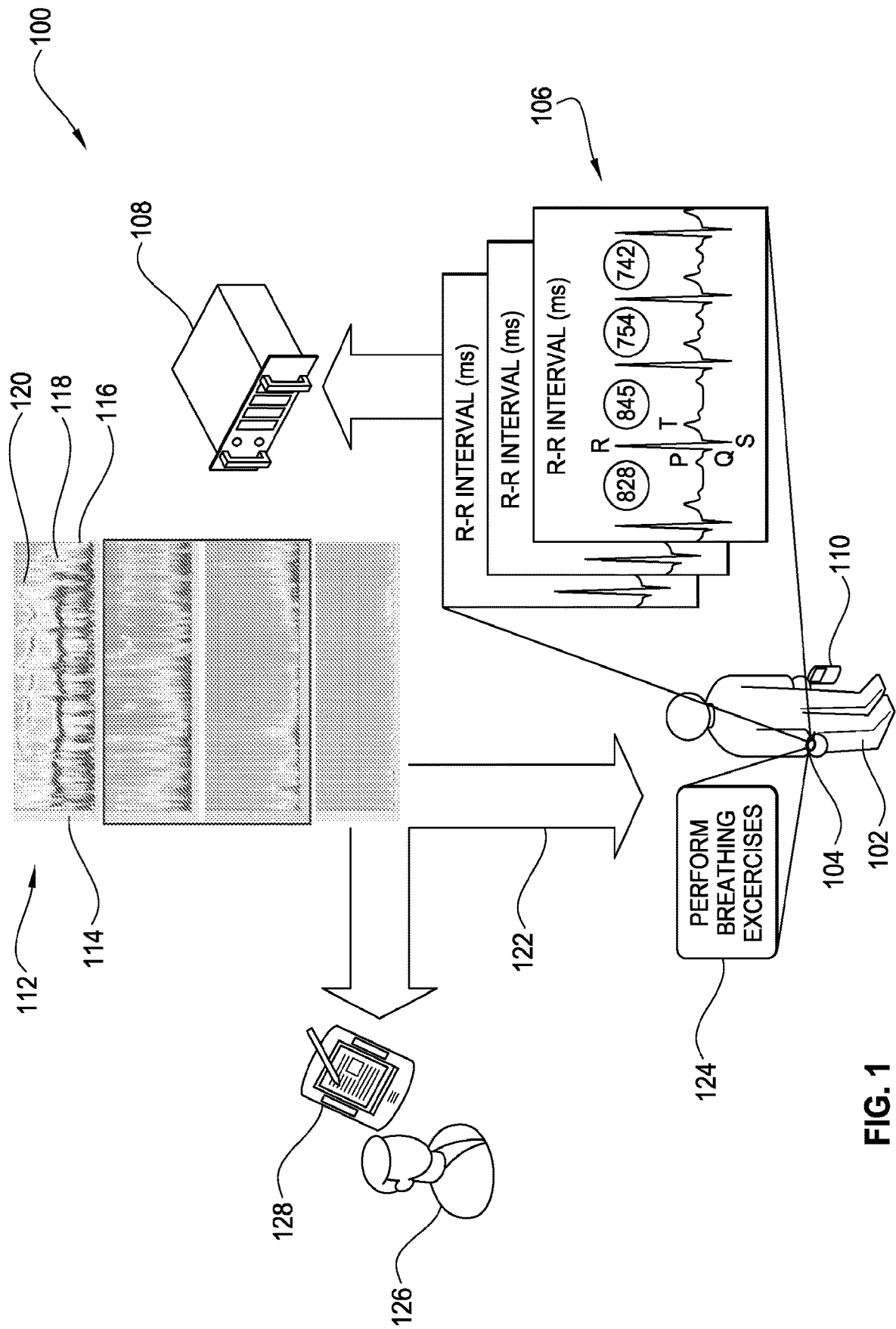
FIG. 1 is a block diagram of a stress dysregulation monitoring platform for a suicidal patient, according to one embodiment.

FIG. 1 shows a system 100 configured to detect, monitor, and intervene on stress dysregulation in a suicidal patient 102, which may be an adolescent, a veteran, or any other at-risk population in some embodiments. Although the present example pertains to HRV for detecting suicidality based on PPG, the concepts described herein are generalizable for using HRV from various sources to monitor a variety of causes of clinical decompensation and recovery ranging from impending cardiac failure to heart re-innervation after a transplant and from over-training (physical and/or mental fatigue) to peaking for an event to depression and improvement upon medical interventions.

Suicide is the second leading cause of death among adolescents, exponentially rising over the past decade, and accounting for more than all other non-mental health diagnoses combined, excluding trauma. Due to the increases in suicidality, parents often utilize emergency departments (ED) to help keep their adolescent safe. A recent nationally representative study found that the number of ED visits for pediatric mental health complaints more than doubled in the most recent decade, now accounting for approximately 1.2 million annual visits. This is a growing problem for EDs as studies have shown that pediatric mental health patients require more resource utilization and have length of stays counted in days, not hours. This becomes an even more complicated situation as up to 20% of unsuccessful adolescent suicide attempts will have a second attempt in 12 months and 45% of pediatric mental health ED patients will have a subsequent visit for a similar complaint. A need exists in adolescent mental health to improve outpatient monitoring and detect worsening symptoms to allow for early interventions before the need for an ED visit. Technology and techniques that empower the patient to monitor and address their symptoms are lacking.

In suicidal patients, it is believed that the balance of the autonomous nervous system is dysregulated, and the parasympathetic nervous system cannot decrease the impulsivity and overdrive of the sympathetic nervous system. One prior study found that patients with a history of suicidality had significantly different HRV values than patients without a history of suicidality. A subsequent study found that energy in the HF component was inversely related to suicidality. This suggests that patients with suicidality may have a heightened sympathetic nervous system that their parasympathetic nervous system cannot downregulate.

Patient 102 is wearing a device such as a smartwatch 104 configured to periodically collect PPG waveform data 106 from patient 102. Smartwatch 104 is, in some embodiments, an Apple Watch available from Apple Inc.; a Fitbit available from Fitbit, Inc.; a smartwatch executing a version of Wear OS available from Google, LLC; or another type of wearable device capable of collecting and providing to other computing devices PPG waveform data 106. A reduced version of waveform data may be used in a tradeoff of local computation power versus transmitted data power.

In one embodiment, smartwatch 104 generates and detects an optical signal using an OSRAM SFH 7070, which includes a combination optical source and detector. The optical source includes two green (635 nm) photodiodes flanking a photodetector. Diode drive current through the two green (635 nm) photodiodes is controlled to change brightness using a Texas Instruments AFE 4044, which also detects the output of the photodetector at 400 Hz using a 23-bit sigma delta converter with ambient light cancellation. Control of current improves SNR, e.g., when no beat is detectable. Any patient-connected source of pulse information may be used within the scope of this disclosure. Other suitable sources of pulse information include: patch sensors (e.g. Cardea Solo from Cardiac Insight), holter monitors (e.g. H3+ Digital Holder Recorder from Welch Allyn), rings (Motive Ring), fitness bands (e.g. Flex Fitness band from Fitbit), smartphone (e.g. iPhone from Apple), non-contact sensors (e.g. RADAR, LIDAR), and continuous monitors, (e.g. CVSM from Welch Allyn), and the like.

PPG waveform data 106 is stored locally on smartwatch 104 and may be subject to optional filtering to ensure optimal data is selected for further processing. For example, analysis software split optical and motion (e.g., accelerometer) data gathered from patients into slightly longer than one-minute segments (e.g., 65 seconds). More generally, a segment is a section of PPG waveform data 106 including a set of sample values obtained for about 60 seconds in duration. Other segment durations may be implemented in some embodiments. Filtering on smartwatch 104 may entail deleting or not acquiring segments of PPG waveform data 106 during excessive movement of patient 102, as detected by corresponding GPS, accelerometers, gyro, magnetic field, or other motion-detecting signals of smartwatch 104. The software will then pick one segment of good data per hour (if possible) with a preference of the chosen segments to be nearest to one hour apart as possible. Thus, as described later in connection with FIG. 2, smartwatch 104 passively monitors HRV and obtains one-minute intervals of clean data (i.e., no motion artifacts) to then calculate HRV metrics. Other interval periods may be implemented in some embodiments. Additional details of segment times are described in Sheridan, David C. et al. "Heart Rate Variability Duration: Expanding the Ability of Wearable Technology to Improve Outpatient Monitoring?" Frontiers in Psychiatry vol. 12 682553. 15 Jun. 2021, which is incorporated by reference.

Available stored segments are uploaded to a server 108 for further processing. Server 108 may be instantiated on a tablet, laptop, smartphone, or other computing device. Motion data may also be provided, depending on whether smartwatch 104 performs filtering or whether it sends all the raw data. Moreover, skilled persons will appreciate that, in other embodiments, a smartphone 110 or local computer may be substituted for a remotely located server 108. In yet other embodiments, all or different portions of processing are performed locally on smartwatch 104. In other examples of processing described later with reference to FIG. 2 and FIG. 4, processing may be performed entirely by smartwatch 104 or among a combination of smartwatch 104 and other computing device(s) including one or both of server 108 and smartphone 110. Distributed computing describes computing solution where multiple processors, such as a processor on a smartwatch and another processor, typically on other devices such as a smartphone, cooperatively analyze and process data.

In some embodiments, processing entails filtering PPG waveform data 106 to remove baseline wander, such as that which occurs due to respiration or motion. Processing also entails detecting beats using the Automatic Multiscale Peak Detection (AMPD) algorithm. Within each segment, the beat picking algorithm, AMPD, is used to determine heartbeats and when each heartbeat occurred. Other beat picking algorithms that reliably pick the heartbeat at the same point in the cardiac cycle may be employed.

Occasionally, server 108 (or other computing device in the system 100) detects an error in the sequence of beat intervals in the AMPD beat picking output. For example, if consecutive beats are temporally spaced apart by 1,000; 1,040; 2,016; and 982 milliseconds, server 108 can determine that the 2,016 gap is likely the result of having missed one beat. As such, the segment is flagged as having an error or artifact, in some embodiments. In a test described in the paper by Sheridan, David C. et al. "Heart Rate Variability Analysis: How Much Artifact Can We Remove?" Psychiatry Investigation, vol. 17, September 2020: 960-965 (which is incorporated by reference), waveforms and beat selections were manually reviewed by a team prior to further analysis to ensure artifact-free data. System 100 includes the ability to find and remove a single beat (or multiple beats) having a motion artifact and determine if it is statistically and clinically acceptable to remove that beat information from the data set.

In some embodiments, analysis software attempts to salvage one minute (60 seconds) or more from a 65 second segment of good data containing a brief segment of bad data, by removing beat intervals in the segment of bad data and concatenating the remaining two large segments of good data. That capability allows the researcher to use more of the good data captured by smartwatch 104 that would otherwise be discarded due to having one artifact. For implementations that use different segment lengths and for different clinical applications, the acceptable duration of bad data may be different. For example, HF and LF measures are affected differently by removal of a beat. In another example, if the factor being measured is strong, data may remain clinically significant with more missing beats.

The thresholds of removing artifact from a 60-65 second segment for each metric is as follows. For Root Mean Square of Successive Differences (RMSSD): Mean absolute percent difference stays below 5% when beats were randomly shifted by 5 samples and when every other beat was shifted to the right up to 5 samples. Increasing every-other-other beat-to-beat interval (BBI) (decreasing the interleaved BBIs) has more effect than random changes in the BBI. Mean absolute percent difference was below 5% when a percentage of beats are removed up to 36% of beats. This was true for both random removal and consecutive removal. For Standard Deviation of NN intervals (SDNN) where 'NN' means next normal: Mean absolute percent difference stays below 5% when shifted until 3 samples have been altered. This was true for both a random shift versus a shift only to the right. Mean absolute percent difference is always below 5% when beats removed up to 36% of beats. This was true for random beat removal and consecutive removal. For mean number of times in which the difference in NN intervals is greater than 50 milliseconds (pNN50): pNN50 is very sensitive to beat shifting. Any amount of shifting, whether random or right only, pushes average absolute percent difference to more than 5%. Mean absolute percent difference is below 5% until 4% of BBI were removed. This is true for both random and consecutive beat removal. For Low Frequency (LF): LF is very robust to shifting BBI right. Mean absolute percent difference stays below 5% until 6 random beats were shifted and then increased. There was no amount of shift to the right that makes the mean absolute percent difference rise above 5%. LF is very sensitive to beat removal with the mean absolute percent difference only staying below 5% when 2% of beats are removed. This is true for both random and consecutive beat removal. For High Frequency (HF): Mean absolute percent difference stays below 5% for beat shifting until 2 samples of random shift. For a right shift, the mean absolute percent difference remains below 5% until 8 samples shifted. HF is very sensitive to random beat removal with the mean absolute percent difference always being greater than 5% with any amount of beats removed. However, for beats removed consecutively the mean absolute percent difference stays at or below 5% until 8% of beats removed.

Of the remaining segments, there might be about 20 measured in a particular hour. To select the optimal one of these 20, with a goal of obtaining one optimal segment for every 60 minutes, each segment is given a score based on the number of errors it has and how far it is temporally from being exactly 60 minutes after the prior segment and exactly 60 minutes before the following segment. For every minute away from 60 minutes spacing, the score is increased by one; for every error, the score is also increased by one. Other scoring systems, including non-linear methods may be used. Server 108 then selects the waveform with the lowest score. In the event no perfectly clean data is available, system 100 identifies the best (lowest noise) sections of data, and optionally cleans sections of data while maintaining the clinical and statistical integrity of the data.

The selected waveform transformed into a tachogram, where the Y axis represents the beat-to-beat interval and the X axis represents time. The PPG tachogram is then converted to PPG frequency data 112 using a Fourier transform. By completing this process repeatedly and color coding the amplitudes, a periodogram is formed. Periodograms are useful in visualizing the change in energy at different frequencies over time. Four examples of continuous PPG frequency data 112 are represented as HRV periodograms, in which the Y axis is in Hertz, the X axis is time (24 hours), and power spectral density is color coded. The data processing instructions to convert BBI data to spectrograms may be achieved using software libraries such as are available Matlab signal processing toolbox or Python using hrvanalysis.py. Skilled persons will appreciate, however, that other representations or data structures may embody the frequency-domain data.

A top plot 114 corresponds to a healthy patient and clearly shows spectral power in very low frequency (VLF) band 116, low frequency (LF) band 118, and high frequency (HF) band 120. The three lower plots show (regressively) unhealthier patients. The ranges (in Hertz) for each band are calculated in hrvanalysis.py as follows: the VLF range is 0.003-0.04 Hz, the LF range is 0.04-0.15 Hz, and the HF range is 0.15-0.40 Hz. Other ranges are possible.

In response to the HF level falling below a threshold level as explained in the paper titled, "Heart Rate Variability and its Ability to Detect Worsening Suicidality in Adolescents: A Pilot Trial of Wearable Technology?" by Sheridan, David C. et al., Presented at: Pediatric Academic Society Conference, May 3, 2021, accepted and in press for Psychiatry Investigation, 2021 (which is incorporated by reference), server 108 will generate and communicate a message 122 for smartwatch 104 (e.g., a push notification), causing it to display dialog 124 and thereby notify patient 102 and direct them to therapeutic coping strategies developed by a patient, caregiver, or licensed provider 126. Other thresholds are appropriate for other patient issues, for example, when considering a patient impending heart, liver, or kidney failure.

A coping mechanism or coping strategy is used to decrease parasympathetic dysregulation, thereby decreasing the probability that of escalation of suicidal ideation. A user-interface of smartwatch 104 allows selection of several typical coping mechanisms, e.g., deep breathing, think of your happy place, and may allow for the addition of patient-specific coping mechanisms, e.g., imagine walking on the beach. Some embodiments provide for playback of favorite songs, images, or videos, all of which are available for selection through the coping mechanism selection user interface. Over time, system 100 learns what coping mechanisms are most likely to be effective for a person with a particular history and ethnographic background and will populate the typical coping mechanism menu with examples that have shown success for a patient with similar environmental factors. A caregiver (caregiver includes anyone charged with caring for the person including psychologist, psychiatrist, therapist, family, friends, licensed clinician, etc.) may also provide inputs that adapt the configuration of the device, including thresholds, limits, filters, and coping mechanism. Analogously, for depression, the effectiveness of a medication and/or working with a therapist can be measured quantitatively using this invention. For a fitness athlete, an accurate measure of HRV provides the system a way to determine what modalities result in the fastest recover. In cardiology, HRV decreasing below a threshold indicates that a patient is likely to have a myocardial infarction. Exercise, improved diet, medications, and surgical interventions may all improve cardiac circulation and health, and the results of each of these can be measured during HRV.

In some embodiments, when server 108 calculates and detects a square root of the HF HRV band 120 decreases (e.g., changes) by about 5 ms/√Hz, it will notify patient 102 of increasing stress dysregulation and instruct him or her to employ coping strategies patient 102 has obtained in consultation with their therapist/provider 126. Note, a limit of about 5 ms/√Hz is equivalent to a limit of 25 ms²/Hz. Using the HF energy or the square root of the HF energy are both considered in this disclosure. Data in the paper titled "Heart Rate Variability and its Ability to Detect Worsening Suicidality in Adolescents: A Pilot Trial of Wearable Technology?" shows that a decrease in square root of HF component by 6.908 can be used to distinguish patients with a Columbia Suicide Severity Rating Scale (CSSRS) value of >15 from those with lower scores (the higher the score, the worse suicidality) (p=0.078). The technology may include the specific coping mechanism that can be programmed by the patient, e.g., perform breathing exercises for 10 minutes or other coping mechanisms. Coping mechanisms may be guided by a clinician and/or programmed by a clinician.

In most of this disclosure, the change in the square root energy in the HF band provides the pertinent information. For a new patient, it is helpful to discriminate between higher-risk and lower-risk patients. These values are dependent on the specific patient population. For example, a population may be divided between those with a CSSRS greater than or equal to 15 and those with a score less than 15. A lower score indicates less risk. For example, the average square root HF value for higher-risk patients might be 7.2 and the average square root HF value for lower risk patients is 12.7 ms/√Hz. In this example, a patient initially measured with a square root of HF value being below 7.2 would be considered at higher risk and a patient initially measured with a square root of HF value being above 12.7 would be considered at lower risk.

In some embodiments, dialog 124 is provided via a user interface that asks the patient directly if they are feeling suicidal at the time of a notification and asks them to rate on a Likert 1-10 scale (1 being the least thoughts of suicidality and 10 being very suicidal). Other scales may be used. The dialog may prompt for feedback at other times, for example before and after a coping mechanism is used. This allows training and feedback to a machine learning algorithm to improve the sensitivity/specificity of the HRV analysis and notification algorithms so that they can become attuned to an individual's personalized thresholds, needs, and preferences. Dialog 124 may be presented over many interfaces including smart TVs, smart cars, smartwatches, smartphone, computers, tablets, and the like. Based on the user feedback and measurements of the patient state, system 100 may adapt limits, thresholds, and filters to provide a personalized solution for the user. Other feedback from the user includes the user's measured physiological state, the user's physiological response time to interventions, and the trend in the patient state, for example becoming more or less dysregulated.

Smartwatch 104 is configured to monitor the coping strategies and provide therapeutic biofeedback about whether patient 102 is showing improvement. If they are showing improvement, it will positively encourage that improvement until they return back to or reach a baseline. If, however, they are showing further dysregulation, it will notify them and then send a message to an identified loved one that was programmed at the time of registration. Patient 102 may be prompted at each notification to rate their suicidality. This allows for improvements of machine learning algorithms to continuously improve test characteristics. For example, after 15 minutes, smartwatch 104 will again perform the HRV measurements. If system 100 calculates and detects a square root of the HR band 120 improvement (increase) of 5 ms/√Hz, it will notify patient 102 of observing significant improvement in their stress and to continue. If the platform detects improving HF band 120, but does not detect the 5 ms/√Hz improvement, it will notify patient 102 to continue their coping mechanisms and encourage them that they are showing improvement. If system 100 detects further decreasing of HF band 120, it will notify patient 102 to continue their coping mechanisms and discuss with loved one or provider. System 100 will utilize smartwatch 104 or a smart phone it is paired with to send a message to an identified loved one using contact information programmed at the time of registration of the platform.

The aforementioned change threshold of 5 ms/√Hz is derived empirically from statistically significant clinical data for detecting patients having a 25% decrease in their CSSRS (i.e., improved suicidality) when the square root of their HF component improves by 5.814 (p=0.001). In some embodiments, the threshold level may be controlled based on age, sex, prior suicidality, sexual orientation, and other parameters (see, e.g., covariates listed in Table 2 of the paper titled "Heart Rate Variability and its Ability to Detect Worsening Suicidality in Adolescents: A Pilot Trial of Wearable Technology?") programmed into system 100 and utilized in the algorithms for analysis. In other words, system 100 performs the above analysis by controlling for the following (some will be programmed in the platform when the patient registers it): hour of day, sex, age in years, prior SI, and circadian rhythm. As described in the attached appendices, the analysis and thresholds described above are guided by controlling for these measures as they significantly alter the data if not controlled for. The specific HRV metric or metrics that are the strongest factors in modelling patient outcomes may vary depending on type of dysregulation.

System 100 facilitates providing guidance and support to patient 102 and the patient's care team provider 126 based on input from patient 102 and the patient's clinical team provider 126. The data and feedback, which may be a retrievable through cloud-based SaaS tools, provide just-in-time therapies, is continuously logged, and will be available for providers in the future to access. For example, FIG. 1 shows a tablet computer 128 available to provider 126 for viewing data system 100 logs, which includes the notifications patient 102 receives with a timestamp and data regarding or noting improvement, decompensation, and other feedback. This information is stored and can be called up by provider 126 or a parent to help them view potential areas where care can be provided.

Logging the data allows for determining specific time points of intervention. For example, if the system 100 detects the patient had notifications every day near 2:00 PM, the care team can then investigate and target therapeutics at that time of day; it may turn out to be a stressful situation patient 102 did not realize they were in. And therapeutic and biofeedback may be rapidly provided to patient 102 at home to help them monitor their own suicidal behavior and intervene. Thus, system 100 has very low friction, i.e., a low resistance to using system 100 compared to other systems that require patients to manually enter data into a smartphone. Furthermore, system 100 does not raise the privacy concerns that are associated with systems that record and analyze conversations. Similarly, the system may include a diary feature where the patient is prompted to provide information when significant changes in the HRV occur. Correlating changes in HRV to specific events, such as meditation, exercise, medication, personal interactions and the like provide the patient and caregivers tools to improve care and outcomes.

Figure 2:
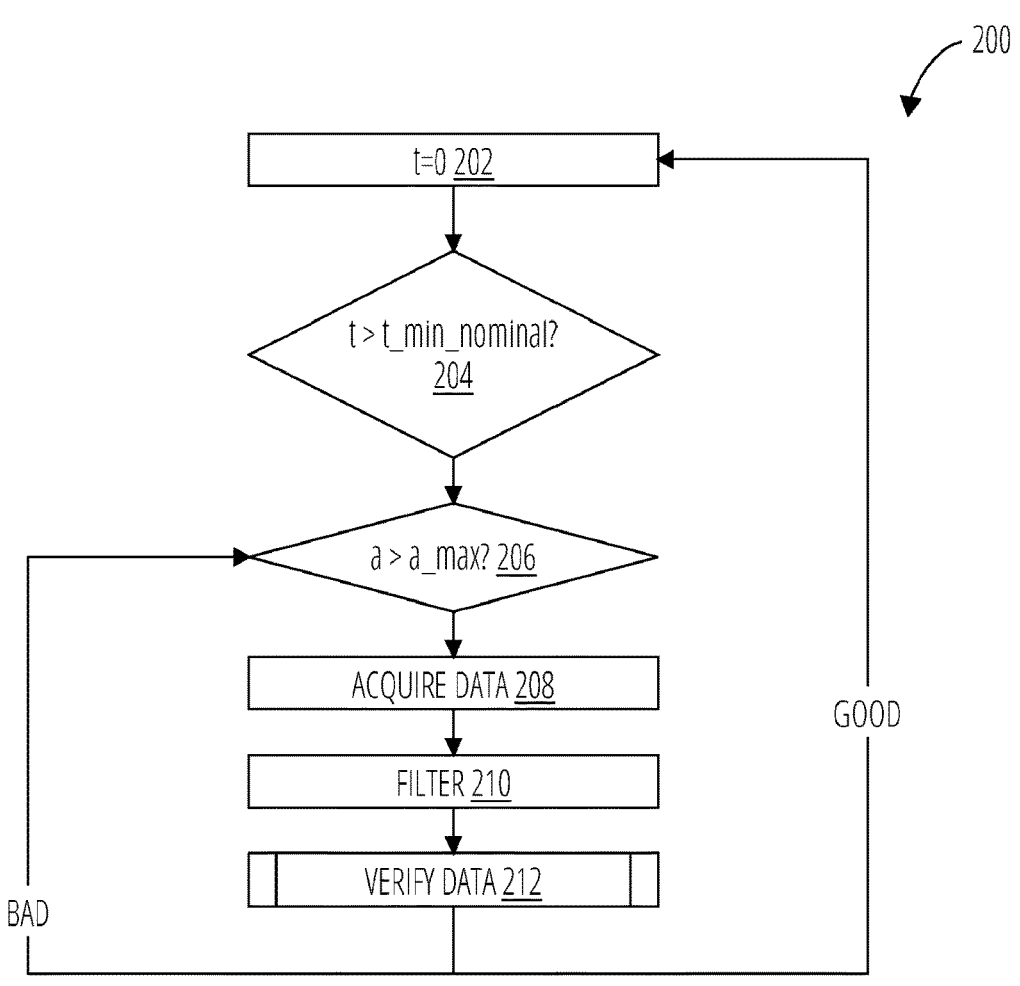
FIG. 2 is a flow chart of a process for collecting and verifying HRV data, according to one embodiment.

FIG. 2 shows a flow chart of a process 200 for collecting HRV data (e.g., PPG waveform data 106, FIG. 1). Initially, it is assumed that valid data is desired nominally every t_min_nominal (minutes) for a duration of t_sec (seconds). The values of t_min_nominal and t_sec might be 60 minutes and 60 seconds, respectively. Because data are sometimes not valid, to help ensure valid data are acquired at least every t_min_nominal interval, data acquisition may begin at an interval that is less than t_min_nominal since the last successful, valid data acquisition. For example, if t_min_nominal=60 minutes and the system has detected a continuous and high amount of patient movement, with a brief cessation at an interval of 50 minutes since the last successful data acquisition, the system may opportunistically acquire data at 50 minutes in case the high motion resumes. If the high motion resumes and continues for more than 60 minutes since the last prior data acquisition, the system has at least obtained data at an interval of 50 minutes. Similarly, the data segment might be acquired for a time longer than t_sec, to help ensure that at least 60 seconds of valid data are acquired. As an example, if a beat occurs at the beginning or the end of the sample, it may not be possible to reliably determine a consistent point in the cardiac cycle at which the beat occurred.

The system can alter the inter-sample interval from a default value of t_min_nominal based on multiple factors including the time since the last PPG waveform data was measured, the quality of the last PPG waveform data (system performance), the patient activity (either derived from examining the PPG waveform to detect motion artifact or derived from a motion detector, such as an accelerometer or gyro). Other factors that influence the interval between intermittently-obtained PPG waveform include the patient state. For example, if the system determines the patient is in an agitated state, it may decrease the inter-sample interval to be less than t_min_nominal. If the patient state is rapidly escalating, it may further decrease the inter-sample interval. The inter-sample interval might be adjusted to measure the effects of a coping mechanism. Similarly, the system may increase the sample length above the nominal t_sec to allow the system to measure the continuous response before, during and after a coping mechanism is applied. The system may have an interface to "sample now" that the person activates when a particularly stressful event occurs. The system may save power and skip measurements (i.e., temporarily halting acquisition) when it detects the person is sleeping or moving, when there is significant activity, or when making accurate physiological measurements is otherwise hampered by a motion artifact. The system may learn what time the person typically awakes and make measurements just before and just after waking. Similarly, the system may learn at what times of the day or day of the week the activity of the parasympathetic nervous systems seems lower and purposefully make measurements at that time. Assuming the elapsed time since the last measurement is near or larger that t_min_nominal, the system may make one of several modification to improve probability of obtaining a clean waveform: increase the sampling rate, increase the output of the LEDs, apply motion-compensation algorithms, increase the averaging done by the A/D convertor, modify the filters, adjust the DC offset of the A/D convertor, and/or prompt the person to be still for a brief period of time.

Timer is (re)set 202 to zero (or the time since the last data was obtained). Process 200 then waits 204 until t=t_min_nominal. Smartwatch 104 performs a check 206 of accelerometer values to ensure they are less than a threshold, a_max. If so, smartwatch 104 begins to acquire data 208 for a duration of t_sec. It also filters data 210 to remove noise and baseline wander. Smartwatch 104 then attempts to verify integrity of data 212. If the data are valid, then process 200 returns to (re)set 202 or else goes to check 206 accelerometer values.

In some embodiments, verify integrity of data 212 comprises checking that the PPG amplitude (a_PPG) is higher than a_PPG_min. If a_PPG<a_PPG_min, then the SNR is likely too low to detect the pulse. The system may then choose to increase the optical output of the LEDs to increase the measured signal. In this disclosure, detecting a pulse and detecting a heartbeat are considered to be the same. For valid HRV measurements, pulses are acquired and detected at the same point in the cardiac cycle with a resolution of about four ms or better.

In other embodiments, verify integrity of data 212 may also include beat detection performed on the signal obtained in acquire data 208 to verify the BBI is reasonable, e.g., 250 ms<BBI<2,000 ms. Limits for BBI may vary based on age, gender, and may be modified using adaptive algorithms to obtain a best fit for a particular patient. For example, an initial configuration might use the limits of 250 ms<BBI<2, 000 ms. Based on ethnographic factors, including age, weight, gender (males are more likely to commit suicide than females), prior history (patients with prior suicide attempts are at a higher risk), home status (patients with a stable home are less at risk), sexual preference (the LGBTQ population is at higher risk), among others, the configuration may be adapted. For example, a smaller, younger patient tends to have a higher heart rate and a lower BBI, so the limits might be set to 250 ms<BBI<1,000 ms. Other limits may be adjusted using manual or automatic means, including application of adaptive algorithms/machine learning.

In some embodiments, verify integrity of data 212 may include smartwatch 104 performing a comparison between detected beats and a corresponding reference signal designed to determine common fiducials (e.g., recurring detectable peaks) representing a repeating cardiogenic artifact. For example, a second beat detection may be performed on a reciprocal of the derivative (e.g., 1/derivative) of the original signal obtained during acquire data 208. Smartwatch 104 compares the beats selected and BBIs in the reciprocal to those of the original signal to determine whether there are common fiducials in the repeating cardiogenic artifact. If they vary by more than a threshold, then it may be assumed that the data are invalid. In other embodiments, the comparison is achieved using a matched filter or other corresponding reference signal.

In yet other embodiments, verify integrity of data 212 entails using pattern recognition algorithms, including machine learning (ML) to look for beats and noise. Other embodiments include computing a signal energy level and a noise energy level. For example, measuring the noise energy or noise amplitude that exists outside of the physiological passband (approximately 0.1 to 6 Hz). If the signal level outside the passband is large compared with the physiological signal level, this is another indication of a high-noise environment or a low-signal environment.

In another example, because some data are invalid, t_min_nominal might be set to a smaller value to start acquiring data earlier. In the limit, t_min_nominal might be set to zero, resulting in continuous data acquisition; however, for a target of over 60 seconds of valid data every 60 minutes, t_min_nominal might be set to 30 minutes, and if the first attempt fails, the system continues to attempt to acquire valid data. That attempt might last a few minutes or even several hours. If valid data is acquired in a few minutes, for example after a total time of 34 minutes, then t_min_nominal might be set to an intermediate value, such as (60–34)/2=13 minutes. If the total time is hours, then upon detection of valid data, t_min_nominal would be reset to 30 minutes.

In yet another example, the system generates more data as the patient state is determined to be at a higher risk and/or if patient motion has precluded obtaining clean data. For example, the sample rate of PPG waveform data 106 can be dynamically controlled (e.g., increased) to improve beat picking accuracy by an algorithm such as AMPD. Signal strength (and thus the SNR) of the optical signal can also be increased by increasing LED brightness. Other controls include the number of integrations, the filter bandwidth, and the duty cycle of the LED. The controls are modifiable through the AFE4404 control registers, in some embodiments.

When valid data sets are acquired at a higher rate than every t_min_nominal, then, as explained previously in connection with the example of FIG. 1 and later in connection with the example of FIG. 4, additional processes facilitate selecting the optimal data as a function of the desired sampling interval t_min_nominal and the quality of the data.

FIG. 3 shows another method 300 of processing PPG waveform data from a wearable PPG device to detect clinical decompensation in a person wearing the wearable PPG device. In block 302, method 300 entails periodically acquiring the PPG waveform data. In block 304, method 300 entails performing beat detection on the PPG waveform data. In block 306, method 300 entails verifying detected beats by checking motion data measured by the wearable PPG device and comparing the detected beats to a corresponding reference signal configured to determine common fiducials representing a repeating cardiogenic artifact. In block 308, in response to the verifying, method 300 entails calculating a heart rate variability (HRV) metric from the detected beats. In block 310, method 300 entails comparing the HRV metric to a clinical decompensation threshold so as to detect the clinical decompensation in the person. In block 312, in response to detecting the clinical decompensation, method 300 entails providing a notification.

Figure 4:
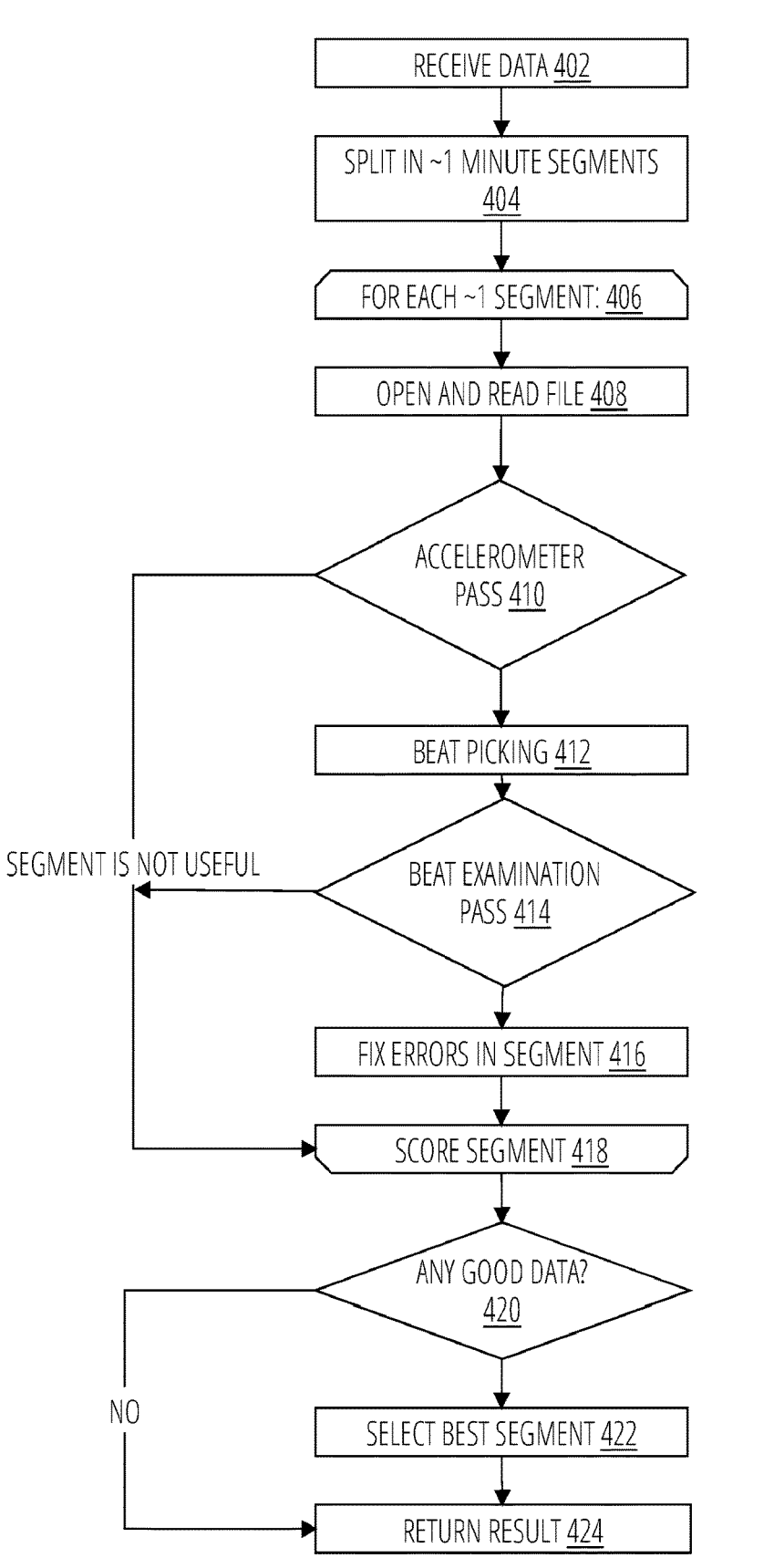
FIG. 4 is a flow chart of a process for scoring and selecting segments of HRV data, according to one embodiment.

FIG. 4 shows a process 400 for selecting an optimal segment for a measurement period. Process 400 may be performed by smartwatch 104, smartphone 110, server 108, or combinations of these computing devices.

Initially, process 400 entails receiving 402 PPG waveform data 106 and accelerometer data. For instance, smartwatch 104 receives this data directly by actuating its optical sensor and detector. In another embodiment, smartphone 110 receives the data through a personal area network, such as a Bluetooth connection. In another embodiment, server 108 receives the data from smartwatch 104 or smartphone 110 through an internet network connection.

Process 400 then entails splitting 404 the received data into segments, which may be t_sec in duration, e.g., about 60 seconds.

For each segment, process 400 entails a subroutine 406, which, in some embodiments includes opening and reading file 408 for a given segment to be analyzed in subroutine 406. Other embodiments need not include opening a file, particularly when PPG waveform data 106 is stored in local memory.

Process 400 then entails checking 410 accelerometer (or other motion) data for excessive movement that would compromise the validity of the given segment. In some embodiments, additional checks are performed. For example, if the waveform's amplitude is less than a defined amplitude threshold, then data is considered bad because the device is picking up noise (e.g., perhaps the device is not even being worn on the patient). If the segment is deemed not useful, then subsequent processing need not be performed in order to save computation.

If the segment is deemed to be useful then beat picking 412 is performed. Beat picking 412 may also be repeated on a reciprocal derivative signal (as described previously) after checking 414 if BPM on filtered data is too low or too high and if the filtered beat picks are too consistent.

In checking 414 the output of beat picking 412, the output is subjected to a beats-per-minute (BPM) filter, according to some embodiments. Data is marked bad if the BPM on the filtered data is too low or too high, e.g., less than 15 to over 200 BPM is not real data. Beat picking on the reciprocal derivative is also skipped if the output is marked as bad.

In some embodiments of checking 414, the output of beat picking 412 is subjected to a consistency filter. Data is marked as bad if the filtered beat picks are too consistent. For example, the data might be saturated, and all beat picks happen at the exact same interval. Real human heartbeat intervals exhibit at least some variability. For example, if all intervals are within three samples of length n, for any n, then the segment is thrown out. Beat picking on the reciprocal derivative is skipped if this is marked as bad.

In some embodiments of checking 414, the output of beat picking 412 is subjected to a beat counts filter. For example, if the number of beats picked varies excessively, for example by more than 15 percent, between the filtered and reciprocal derivative, then the data is marked as bad.

If checking 414 indicates there are fixable errors in the segment, then process 400 entails resolving errors 416. Fixable errors tend to be those introduced in the analysis and computation which are well characterized. Because they are well characterized, they can be identified and remediated. For example, errors may include AMPD picking noise spikes from a known hardware glitch, double picking beats due to overlapping AMPD windows, filling in missing beats that were found in a reciprocal derivative. In the first case, knowledge of the waveform shape allows detection using a matched filter. If the shape of the noise spike and the beat pick are at the same time, the system can conclude the beat pick is non-cardiogenic and discard it. In the second case, as a result of parallel processing, where data are broken into small chunks for faster analysis, there is occasionally a true beat at the edge of the chunk that is detected twice, with an offset of one sample. The second beat may be deleted. Finally, when the beat picking on the original waveform has a sudden doubling in the BBI (indicating a chance that there was a missed beat) and the beat picking based on the derivative detects a beat at the location we expect it (based on the just prior and the next BBIs), it can be concluded that the derivative detector found a beat that should be inserted into the list of beats derived from the original waveform. In general, fixable errors include: a double picked beat, a missed beat, and a small bad segment. A double picked beat occurs when small 15 second segments where AMPD was run are stitched back together into a one-minute segment, and a borderline beat gets picked twice. One of the picks gets removed. A missed beat in filtered can be fixed if the beat was picked in the reciprocal derivative, which it can use instead with offset adjustment. A small bad segment, i.e., 2 intervals or less, can be removed with the surrounding good segments stitched together, keeping at least 60 seconds of good data because we initially picked 65 seconds. Usually, there are no errors of this type needing to be fixed.

Scoring 418 entails calculating a score for a segment. For example, as described previously, segments having fewer fixes and closest to one hour from a last picked segment are given better scores. Subroutine 406 is then concluded.

If there is any useful data 420, then the segment having the best score is selected 422. The selected results are returned 424 for further processing.

FIG. 5 shows a process 500 for providing therapeutic feedback to patient 102. As noted previously, some monitoring and feedback aspects of process 500 may be performed using smartwatch 104 or a combination of smartwatch 104 and smartphone 110. Provider 126 feedback aspects of process 500 may be performed by tablet computer

128. Thus, skilled persons will appreciate that process 500 provides a general overview of separate and discrete processes that may be performed by one or more computing devices shown in FIG. 1.

Initially, a patient receives a notification from an HF band monitoring device 502. Note that other HRV metrics may be used, for example RMSSD (Root mean square of successive differences) is a surrogate for HF; HF energy may be normalized (typically using the LF energy); and other physiological measures may be included, such as respiration rate, blood pressure, galvanic skin response and the like. Use of surrogates for the HF energy calculation are also possible. This might be, for example, because RMSSD requires fewer computational resources than calculating the HF component of HRV. RMSSD, HF energy, HF/LF energy, and, as described below, the standard deviation of width of points perpendicular to the line of identity indicates the short-term variability in a Poincaré plot, are all strongly correlated with each other and with parasympathetic nervous activity. As such, these may be substituted for each other with suitable changes in the limit. When such a device calculates and detects a square root of the high frequency HRV band decrease of 5 ms/√Hz, which indicates a decrease in parasympathetic activity and an increase in suicidal risk, it will notify patient 102 of increasing stress dysregulation and to utilize coping strategies patient 102 has from their therapist/provider 126.

The threshold at which actions, such as alerting the user to utilize coping strategies, occur could be modified from a baseline value knowing that while for the typical population a decrease of 5 ms/√Hz, depending in the effect of ethnographic factors, including those mentioned previously, it may be that for a 16-year-old, obese, LGBTQ male in an unstable home environment, that a decrease of about 4 ms/√Hz is significant. In this example, the threshold would be changed from 5 to 4 ms/√Hz. In contrast, it may be for an 18-year-old female in a stable home environment, that a decrease to about 6 ms/√Hz is significant. In this example, the threshold would be changed from 5 to 6 ms/√Hz. Additionally, as the system obtains more data overall and more data from a specific person, limits for notifications and/or filters may be further adjusted to further personalize the system. If the system may have set a person's BBI filters to 250 to 1,000 ms, but after monitoring the individual, learns that the patient has an unusually low heart rate, the BBI filters might be adapted to values of 375 to 1,600 ms.

As another example, assuming a system with that has a default threshold of 5 ms/√Hz at which is issues a "use coping mechanism," reminder, that the system queries the individual about how he feels before and after the coping mechanism is applied. In a first case, the individual may indicate he feels fine before and after the coping mechanism is applied. In this first case, the system may learn that the threshold is set too low and modify the threshold from 5 to 6 ms/√Hz. In another example, the individual may indicate he feels poorly before and after the coping mechanism is applied. In this example, the system may learn the coping mechanism is inadequate or is inadequately applied. It may adapt to using a different coping mechanism and/or provide coaching on how to apply the coping mechanism and/or may escalate to a care giver. The care giver may manually change the coping mechanisms that are suggested to the individual. Alternately, the system may learn that a set of coping mechanisms together provide the desired result, and provide guidance to use the set of coping mechanisms. In a third case, the individual may indicate he feels poorly before and better after the coping mechanism is applied, and the metrics match this. In this third case, the system may learn it has no need to adapt the algorithms. As a further example, it may be that the HF metric mentioned has a diurnal cycle, perhaps with a morning threshold of 2 ms/√Hz, which increases throughout the day to 8 ms/√Hz. In this case, the system would adapt to include this diurnal variation. Many other physiological metrics, including other HRV metrics may be found upon further research to be significant factors to create a personalized of regulation/deregulation of response that represents a particular person well. This specification antici- pates that other factors will be included with other metrics. Further, some HRV metrics have overlapping influence on the statistical model. That is, there are HRV factors that are well correlated and using these factors together does not improve the model. As an example, RMSSD, which is a time-domain HRV metric is strongly correlated with the HF component of the HRV power spectral density. Substituting correlated metrics considered within the scope of this dis- closure.

In response to the notification and guided coping mecha- nism, the patient tries the coping mechanism 504. After 15 minutes (or other configurable, predetermined period), the device will perform the same HRV measurements to deter- mine 506 whether the patient is improving.

If the platform detects insufficient improvement (e.g., further decreasing energy in the HF band), it will escalate, for example: notify 508 the patient to continue their coping mechanisms and discuss with loved one or provider. The platform will utilize the smart device it is on to send a message to an identified loved one that was programmed at time of registration of the platform.

If the platform calculates and detects a square root of the HF HRV band improvement of 5 ms/√Hz, it will notify 510 the patient of observing significant improvement in their stress and to continue the coping mechanism. Similarly, if the platform detects improving HF band, but does not detect the 5 ms/√Hz improvement (increase), it will notify the patient to continue their coping mechanisms and encourage them that they are showing improvement.

Data is stored 512 on one or both of a computing device and cloud-based system so that patient 102 can review 514 it with provider 126. Provider 126 can then tailor 516 treatment.

Figure 6:
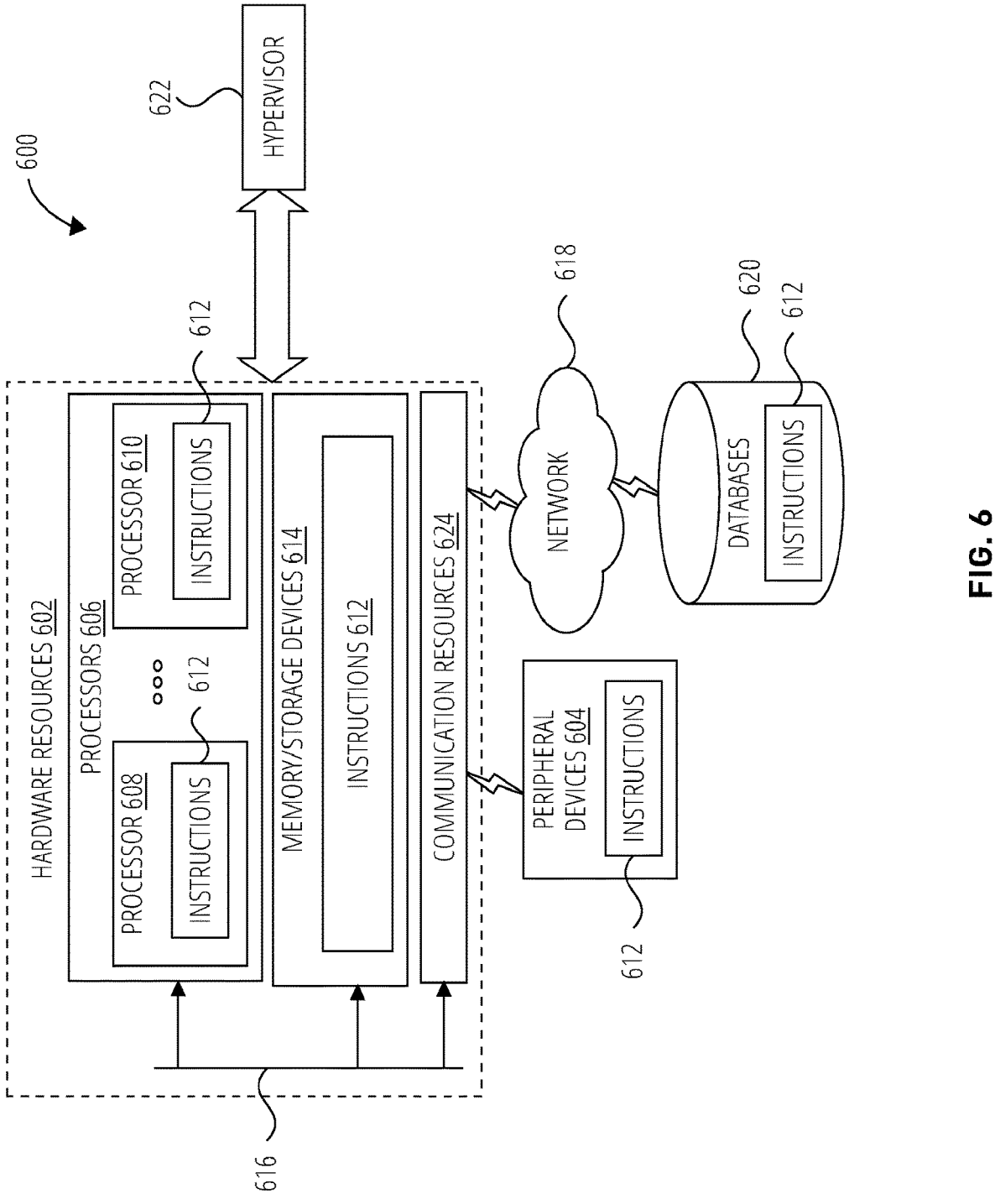
FIG. 6 is a block diagram of a computing device, according to one embodiment.

FIG. 6 is a block diagram illustrating components 600, according to some example embodiments, able to read instructions from a machine-readable or computer-readable medium (e.g., a non-transitory machine-readable storage medium), and perform any one or more of the methodolo- gies discussed herein. For example, hardware resources 602 may be embodied in smartwatch 104, server 108, tablet computer 128, or patient-connected device that provides the ability to measure a physiological signal, provide some analysis of that signal, transmit information about that signal, and/or support a user interface to provide information about that signal. This includes an equivalent functional combination, for example a watch that can measure a physiological signal and transmit the data to a computer (including a smartphone), where the computer provides analysis and user interface functions. Similarly, a smart- phone worn near the heart could detect the heartbeats and provide all the necessary functionality using an audio detec- tor and/or using the built-in LED and camera to capture a photoplethysmogram. A patient-worn physiological moni- toring patch could measure the data and transmit it to a smartwatch, smartphone, or computer.

Specifically, FIG. 6 shows a diagrammatic representation of hardware resources 602 including one or more processors 606 (or processor cores), one or more memory/storage devices 614, and one or more communication resources 624, each of which may be communicatively coupled via a bus 616. For embodiments where node virtualization (e.g., NFV) is utilized, a hypervisor 622 may be executed to provide an execution environment for one or more network slices/sub- slices to utilize the hardware resources 602.

The processors 606 (e.g., a central processing unit (CPU), a reduced instruction set computing (RISC) processor, a complex instruction set computing (CISC) processor, a graphics processing unit (GPU), a digital signal processor (DSP) such as a baseband processor, an application specific integrated circuit (ASIC), a radio-frequency integrated cir- cuit (RFIC), another processor, or any suitable combination thereof) may include, for example, a processor 608 and a processor 610.

The memory/storage devices 614 may include main memory, disk storage, or any suitable combination thereof. The memory/storage devices 614 may include, but are not limited to any type of volatile or non-volatile memory such as dynamic random access memory (DRAM), static ran- dom-access memory (SRAM), erasable programmable read- only memory (EPROM), electrically erasable program- mable read-only memory (EEPROM), Flash memory, solid- state storage, etc.

The communication resources 624 may include intercon- nection or network interface components or other suitable devices to communicate with one or more peripheral devices 604 or one or more databases 620 via a network 618. For example, the communication resources 624 may include wired communication components (e.g., for coupling via a Universal Serial Bus (USB)), cellular communication com- ponents, NFC components, Bluetooth® components (e.g., Bluetooth® Low Energy), Wi-Fi® components, and other communication components.

Instructions 612 may comprise software, a program, an application, an applet, an app, or other executable code for causing at least any of the processors 606 to perform any one or more of the methods discussed herein. The instructions 612 may reside, completely or partially, within at least one of the processors 606 (e.g., within the processor's cache memory), the memory/storage devices 614, or any suitable combination thereof. Furthermore, any portion of the instructions 612 may be transferred to the hardware resources 602 from any combination of the peripheral devices 604 or the databases 620. Accordingly, the memory of the processors 606, the memory/storage devices 614, the peripheral devices 604, and the databases 620 are examples of computer-readable and machine-readable media.

Aside from the energy in the HF component, HRV may be quantified by other metrics and methods of viewing the data that the present inventor believe could provide a measure of suicidality. For example, SDNN is a surrogate for the HF energy. And normalizing to the LF energy is often helpful (HF/LF ratio). In another example, a Poincaré plot is a scatterplot of the current BBI plotted against the preceding BBI. Poincaré plot analysis is a quantitative visual tech- nique, whereby the shape of the plot is categorized into functional classes; it provides summary information as well as beat-to-beat information. Points above the line of identity indicate RR intervals that are longer than the preceding RR interval, and points below the line of identity indicate a shorter RR interval than the previous. The width of points perpendicular to the line of identity indicates the short-term variability. This width can be quantified by the standard deviation of the distances the points lie from the line of identity and is equivalent to the standard deviation of the successive differences of the RR intervals (SDSD or RMSSD). The standard deviation of points parallel to the line of identity (the "length") reflects the standard deviation of the RR intervals (SDNN). Poincaré plots provide an ability to identify beat-to-beat cycles and patterns in data that are difficult to identify with frequency- or time-domain analysis. Deceleration capacity another measure of how well the body can slow-down the heart rate. Accordingly, other physiological metrics with associated ranges and/or limits that provide a measure of suicidality.

Skilled persons will appreciate that many changes may be made to the details of the above-described embodiments without departing from the underlying principles of the invention. The scope of the present invention should, therefore, be determined only by claimed inventions and equivalents thereof.

What is claimed is:

1. A method of processing photoplethysmography (PPG) waveform data from a wearable PPG device to detect clinical decompensation in a person wearing the wearable PPG device, the method comprising:

periodically acquiring the PPG waveform data;

splitting the PPG waveform data into segments;

scoring each segment based on its temporal proximity to a desired time interval for acquiring the segment;

processing PPG waveform data based on one of the segments having a best score based on a number of errors it has and its temporal proximity;

performing beat detection on the PPG waveform data;

verifying detected beats by checking motion data measured by the wearable PPG device and comparing the detected beats to a corresponding reference signal configured to determine common fiducials representing a repeating cardiogenic artifact;

in response to the verifying, calculating a heart rate variability (HRV) metric from the detected beats;

comparing the HRV metric to a clinical decompensation threshold so as to detect the clinical decompensation in the person; and in response to detecting the clinical decompensation, providing a notification.

2. The method of claim 1, in which the HRV metric includes at least one of: HF component, HF/LF ratio, RMSSD, and standard deviation in width of a Poincaré plot.

3. The method of claim 1, further comprising:

determining after a predetermined period whether the HRV metric indicates an improvement to the clinical decompensation; and alerting a third party in response to insufficient improvement.

4. The method of claim 1, in which the providing the notification includes indicating an intervention.

5. The method of claim 1, in which the providing the notification includes generating a message to cause the wearable PPG device to notify the person or a caregiver of a risk of suicidality.

6. The method of claim 1, in which the wearable PPG device has a smartwatch form factor.

7. The method of claim 1, further comprising providing the PPG waveform data to a remotely located server configured to process the PPG waveform data.

8. The method of claim 1, further comprising scoring each segment based on beat picking errors.

9. The method of claim 1, further comprising:

detecting a sequence of beat intervals in the PPG waveform data; and removing errors in the sequence.

10. The method of claim 1, further comprising temporarily halting the periodically acquiring when the motion data indicates the person was moving.

11. The method of claim 1, further comprising filtering the HRV metric to remove a portion acquired while the motion data indicates the person was moving.

12. The method of claim 1, in which the clinical decompensation indicates a decline in mental health.

13. The method of claim 1, in which the intervention comprises an activity that does not require participation of a clinician.

14. The method of claim 13, in which the intervention comprises one of therapeutic biofeedback or a personalized solution for the user.

* * * * *